United States Patent [19]
Puckette et al.

[11] Patent Number: 5,591,874
[45] Date of Patent: Jan. 7, 1997

[54] PROCESS FOR THE PREPARATION OF 2,5-DIHYDROFURAN COMPOUNDS

[75] Inventors: Thomas A. Puckette; Gerald W. Phillips, both of Longview, Tex.

[73] Assignee: Eastman Chemical Company, Kingsport, Tenn.

[21] Appl. No.: 536,595

[22] Filed: Sep. 29, 1995

[51] Int. Cl.$^6$ ............... C07D 307/28; C07D 307/78
[52] U.S. Cl. ........................... 549/507; 549/355
[58] Field of Search ..................... 549/507, 355

[56] References Cited

U.S. PATENT DOCUMENTS

| | | | |
|---|---|---|---|
| 5,034,545 | 7/1991 | Fischer | 549/507 |
| 5,082,956 | 1/1992 | Monnier et al. | 549/507 |
| 5,238,889 | 8/1993 | Falling et al. | 549/507 |
| 5,315,019 | 5/1994 | Phillips et al. | 549/507 |
| 5,466,832 | 11/1995 | Tustin | 549/507 |

FOREIGN PATENT DOCUMENTS

| | | | |
|---|---|---|---|
| 1177877 | 1/1970 | United Kingdom | 568/867 |
| 2023601 | 1/1980 | United Kingdom | 568/867 |
| 2098985 | 12/1982 | United Kingdom | 568/867 |

OTHER PUBLICATIONS

T. Fujinmai, T. Suzuki, M. Kamiya, *Tetrahedron Letters*, 199 (1985).

Ogako, Y., Takeda, M, Jpn. Kokai Tokkyo Koho JP 02,282, 382 (90,282,382)—(Chem. Abs. 114:143400p). (1991).

Rinz, J., Paparizos, C., and Herrington D., Eur. Pat. Appl. EP 69,494—(Chem. Abs. 98:198193e). (1983).

Y. Rujita, T. Morimoto, T. Nakanoichi, Japan 73 22,702, 07 Jul. 1973—Chem. Abs. 146007k).

Y. Fujita, T. Morimoto, T. Nakano, Japan 72 26,786, 19 Jul. 1972—(Chem. Abs. 139451f).

*Primary Examiner*—Joseph E. Evans
*Attorney, Agent, or Firm*—J. Frederick Thomsen; Harry J. Gwinnell

[57] ABSTRACT

Disclosed is a process for the preparation of 2,5-dihydrofuran compounds by contacting an olefinically-substituted ethylene carbonate compound with a catalyst comprising an acidic component and a halogen component. The process is especially useful for the preparation of 2,5-dihydrofuran from vinyl ethylene carbonate (4-ethenyl-1,3-dioxolane-2-one) which is readily available from 3,4-epoxy-1-butene.

11 Claims, No Drawings

PROCESS FOR THE PREPARATION OF 2,5-DIHYDROFURAN COMPOUNDS

This invention pertains to a process for the preparation of 2,5-dihydrofuran compounds by contacting an olefinically-substituted ethylene carbonate compound with a catalyst comprising an acidic component and a halogen component. The process is especially useful for the preparation of 2,5-dihydrofuran from vinyl ethylene carbonate (4-ethenyl-1,3-dioxolane-2-one) which is readily available from 3,4-epoxy-1-butene.

The preparation of 2,5-dihydrofuran compounds is well known in the literature. The manufacture of 2,5-dihydrofuran is of commercial interest since many valuable products such as tetrahydrofuran, 1,4-butane-diol, butyrolactone, and N-methylpyrrolidinone can be prepared from this versatile intermediate. The synthesis of 2,5-dihydrofuran compounds by the isomerization of 3,4-epoxy-1-butene utilizing iodide-containing catalysts is described U.S. Pat. Nos. 3,932,468, 3,996,248, 5,034,545, 5,082,956 and 5,315,019. The preparation of 3,4-epoxy-1-butene and related compounds by the selective monoepoxidation of dienes such as butadiene is described in U.S. Pat. Nos. 4,897,498 and 4,950,773.

The present invention avoids many of the problems associated with working with highly reactive, volatile, organic chemicals such as 3,4-epoxy-1-butene. Epoxides in general are highly reactive compounds and react with great facility under acidic or basic conditions (Organic Chemistry, 3rd Edition; Morrison and Boyd, pages 562–565). Epoxides must handled with caution to prevent contamination and the possibility of an uncontrolled, decomposition reaction. Vinyl substituted cyclic carbonates do not have the strained three member ring of an epoxide and are much less sensitive to contamination by acids, bases or water. As a result the carbonates are safer to ship and store than the unsaturated epoxides.

Exposure to the vapors or liquids of reactive chemicals is a continuing concern in the chemical industry. The unsaturated epoxides often are much more volatile than the corresponding vinyl substituted carbonates. As a result, the possibility of exposure to vapors is reduced by the use of the cyclic carbonate in place of the epoxides. In accordance with the process of this invention, cyclic carbonates can now be utilized in place of the unsaturated epoxides to manufacture the same derivative compounds in a safer work environment. A valuable feature of the present invention is that cyclic carbonates may serve as masked or stabilized epoxyalkenes. The cyclic carbonates are compounds which are much less volatile, more stable, and yet are sufficiently reactive to allow the transformation of the carbonate to products such as 2,5-dihydrofuran.

The cyclic carbonates are readily prepared by the reaction of carbon dioxide with unsaturated epoxides such as epoxyalkenes, e.g., 3,4-epoxy-1-butene, in the presence of a variety of catalysts according to known procedures. The use of palladium catalysts such as tetrakis(triphenylphosphine)palladium(O) has been reported by Fujinami et al. [T. Fujinami, T. Suzuki, M. Kamiya, *Tetrahedron Letters*, 199 (1985)] and Ogako et al. [Ogako, Y., Takeda, M, Jpn. Kokai Tokkyo Koho JP 02,282,382 (90,282,382); (Chem. Abs. 114:143400p)]. Halide-containing catalysts such as tantalum chloride also have been reported by Rinz et al. [Rinz, J., Paparizos, C., and Herrington D., Eur. Pat. Appl. EP 69,494]. The use of phosphines as the catalyst has been reported by Fujita et al. [Y. Fujita, T.. Morimoto, T. Nakanoichi, Japan 73 22,702, 07 Jul. 1973] who teach the preparation of vinyl ethylene carbonate by the reaction of the 3,4-epoxy-1-butene with carbon dioxide at a temperature of 190° C. and a pressure of 113 bars absolute (115 Kg/cm², 1635 pisa) using only tricyclohexylphosphine as the catalyst.

The rearrangement of vinyl ethylene carbonate is discussed briefly by Fujinami and coworkers in a paper published in *Tetrahedron Letters*, 199 (1985) which describes the preparation of the carbonate from 3,4-epoxy-1-butene. Fujinami reports (page 199, paragraph 3, lines 2–5) that:

"When the reaction mixture was refluxed for 2 h, 2 (vinyl ethylene carbonate) was completely converted to the decarboxylated isomerization products, 3-butenal and an unidentified viscous material which had no absorption band of cyclic carbonate in the IR spectrum."

Fujinami comments further in the notes at the end of the paper about additional reactions of vinyl ethylene carbonate. Note 7 states " . . . vinylethylene carbonate2 reacted with nucleophiles in the presence of (Ph₃P)₄Pd to produce hydroxybutenyl derivatives . . . ".

Fujita and coworkers (Y. Fujita, T.. Morimoto, T. Nakano, Japan 72 26,786, 19 Jul. 1972) describe the preparation of vinyl ethylene carbonate by the reaction of epoxy butene with CO₂ in an autoclave using halide salts of chromium, manganese, ruthenium, rhodium or cadmium in the presence of tertiary phosphines which serve as promoters for the reaction. Manganese bromide is given as a preferred catalyst for this reaction. The product reported for this reaction by Fujita is vinyl ethylene carbonate and not dihydrofuran.

It has been found that vinyl-substituted cyclic carbonates can be isomerized to form 2,5-dihyrofuran compounds in high selectivity and high yield. Contacting the vinyl-substituted cyclic carbonate with a catalyst comprising a component with either Lewis or protic acidity and a component containing a halogen results in the formation of the desired 2,5-dihydrofuran in high yield and selectivity. The present invention therefore provides a process for the preparation of 2,5-dihydrofuran compounds having the formula:

which comprises contacting vinyl ethylene carbonate compounds having the formula

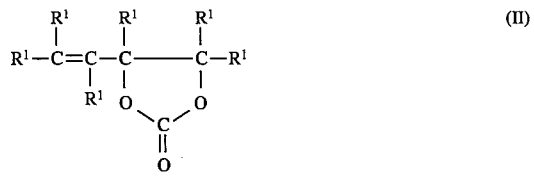

with a catalyst system comprising an acidic component and a halogen component;

wherein each $R^1$ is independently selected from hydrogen, alkyl of up to about 8 carbon atoms, a carbocyclic or heterocyclic aryl group of about 5 to 10 carbon atoms or halogen or any two $R^1$ substituents collectively may represent an alkylene group forming a ring, e.g., alkylene containing in the main chain 4 to about 6 carbon atoms. The preferred 2,5-dihydrofuran products and vinyl ethylene carbonate reactants comprise compounds of formulas (I) and (II) wherein the $R^1$ substituents individually represent hydrogen, lower alkyl, e.g., alkyl of up to about 4 carbon atoms, or halogen or collectively represent straight or branched chain alkylene of 4 to about 8 carbon atoms, especially compounds of formulas (I) and (II) wherein at least 4 of the $R^1$ groups represent hydrogen. Exemplary reactants contemplated for use in the practice of the present invention include 4-ethenyl-1,3-dioxolane-2-one, 4-ethenyl-5-ethyl-1,3-dioxolane-2-one, 4-(1-butenyl)-1,3-dioxolane-2-one, 4-ethenyl-5-methyl-1,3-dioxolane-2-one, 4-(1-propenyl)-1,3-dioxolane-2-one, 4-ethenyl-5-phenyl-1,3-dioxolane-2-one and the like. The reactant of primary interest is 4-ethenyl-1,3-dioxolane-2-one.

The present process utilizes a catalyst comprising an acidic component and a halogen component. The acidic component may be selected from compounds with either Lewis or protic acidity. The Lewis acid compounds may be selected from compounds containing elements from Group IIA, IIB, IIIA, IIIB, IVA, IVB, VA, VB, and the transition metals (Groups VIB, VIII, and IB) of the periodic table. Compounds containing elements from the Lanthanide and Actinium series may also be successfully used as the acidic component of the catalyst. The anion component of the Lewis acidic compounds may be selected from a wide variety of common anions such as carboxylates, e.g., acetate, oxides, nitrates, sulfates and halides. The preferred Lewis acid catalyst components are the halides, e.g., chlorides, bromides and iodides, of calcium, zinc, tin, manganese, uranium, aluminum, cerium, magnesium, thorium, zirconium, copper and chromium.

Examples of such Lewis acid catalyst components include the alkali metal halides, zinc halides, magnesium halides, tin (II) halides, tin (IV) halides, titanium (IV) halides, titanium (IV) tetra-lower-alkoxides, zirconium (IV) halides, manganese (II) halides, iron (III) halides, or iron (III) acetylacetonate. Preferably, the Lewis acid component is an alkali metal iodide, zinc iodide, zinc chloride, magnesium iodide, tin (II) iodide, tin (IV) iodide, titanium (IV) iodide, titanium (IV) tetramethoxide, titanium (IV) tetraethoxide, titanium (IV) tetraiso-propoxide, zirconium (IV) iodide, manganese (II) iodide, manganese (II) chloride, iron (III) iodide, iron (III) acetylacetonate or a combination thereof. The Lewis acid catalyst components which are particularly preferred are polarizable iodides, such as, for example, titanium (IV) iodide, zirconium (IV) iodide, and, especially, zinc iodide and tin (II) iodide.

The Lewis acid component alternatively may be selected from organotin (IV) and organoantimony (V) compounds such as hydrocarbyltin trihalides, dihydrocarbyltin dihalides, trihydrocarbyltin halides, dihydrocarbylgermanium dihalides, trihydrocarbylgermanium halides, tetrahydrocarbyltin compounds and tetrahydrocarbylantimony halides. Examples of such organometallic compounds include compounds having the formulas

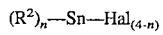

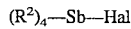

and

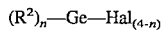

wherein each $R^2$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms;

Hal is a halogen atom such as bromo or, preferably, iodo; and n is 1, 2, 3 or 4.

Examples of organometallic compounds include dibutyltin diiodide, tributyltin iodide, trioctyltin iodide, triphenyltin iodide, tributyltin bromide, trimethyltin iodide, butyltin triiodide, tetrabutyltin, tetraoctyltin, triphenyltin iodide, tribenzyltin iodide, dimethyltin diiodide, diphenyltin diiodide, triphenyltin bromide and tetraphenylantimony iodide.

The preferred organometallic compounds comprise tin (IV) iodides having the above general formula and a total carbon content of about 3 to 36 carbon atoms wherein each $R^2$ substituent independently is selected from alkyl of up to about 12 carbon atoms, benzyl, phenyl or phenyl substituted with up to 3 substituents selected from lower alkyl, lower alkoxy or halogen;

Hal is iodo; and n is 2 or 3.

The acid component of the catalyst may be selected from inorganic acids such as mineral acids, e.g. sulfuric, hydrochloric, hydrobromic, and hydroiodic acids; phosphoric acid, polyphosphoric acid, perchloric acid or nitric acid. Strong organic acids such as carboxylic acids containing up to about 4 carbon atoms, e.g., oxalic, acetic, and formic acid; and sulfonic acids, e.g., alkyl- and aryl-sulfonic acids containing up to about 8 carbon atoms, also may be used as the acid component of the catalyst.

The halogen component of the catalyst may be selected from a large number and variety of inorganic and organic, halogen-containing compounds. The halogen may be chlorine, bromine or iodine although bromine or iodine are preferred and iodine is the most preferred halogen or halide. Examples of inorganic halogen compounds include the chlorides, bromides and iodides of the elements set forth above in the description of the Lewis acids which may constitute the acid component of the catalyst. The alkali metal bromide and, especially, the alkali metal iodides such as lithium, sodium, potassium and cesium iodides, are the preferred inorganic halogen compounds. The acid component and halogen component of the catalyst system utilized in the present invention normally comprise at least 2 distinct chemical compounds.

The halogen component may bean organic halogen-containing compound such as an onium halide salt, e.g., a tetravalent nitrogen, phosphorus, arsenic, antimony and bismuth compounds. Examples of the onium halides are compounds conforming to the formulas

 (III)

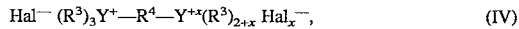 (IV)

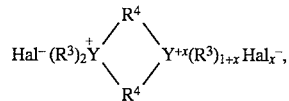 (V)

or

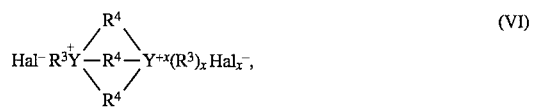 (VI)

wherein each $R^3$ independently is selected from hydrogen, alkyl or substituted alkyl moieties having up to about 20 carbon atoms, cycloalkyl or substituted cycloalkyl having about 5 to 20 carbon atoms, or aryl or substituted aryl having about 6 to 20 carbon atoms; or when Y is P, each $R^3$ also may be selected from alkoxy of up to about 20 carbon atoms, cycloalkoxy of about 5 to 20 carbon atoms, aryloxy of 6 to 10 carbon atoms or halogen;

two or three $R^3$ substituents collectively may represent joined hydrocarbylene groups, e.g. alkylene having 4 to 6 main chain carbon atoms or unsaturated groups such as —CH=CHCH=CHCH= and lower alkyl substituted alkylene and unsaturated groups, which form a mono- or poly-cyclic ring with the Y atom to which they are bonded;

each $R^4$ is independently selected from hydrocarbylene moieties or substituted hydrocarbylene moieties;

x is 0 or 1;

Y is N, P or As; provided that the quaternary onium iodide compound contains at least 6 carbon atoms; and Hal is chloro, bromo or iodo.

The substituted groups and moieties referred to above bear one or more substituents such as groups having the formulas

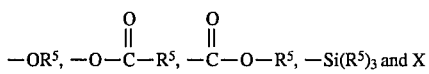

wherein each $R^5$ is independently selected from hydrogen or alkyl of up to about 20 carbon atoms and X is halogen. As used herein, the terms "hydrocarbylene moieties" refers to alkylene moieties having up to about 6 carbon atoms, arylene or polyarylene moieties having 6 to 20 carbon atoms.

The preferred onium halide catalysts are the quaternary ammonium and quaternary phosphonium bromide and, especially, iodide compounds. Exemplary ammonium compounds include tetra-pentylammonium iodide, tetrahexylammonium iodide, tetraoctylammonium iodide, tetradecylammonium iodide, tetradodecylammonium iodide, tetrapropylammonium iodide, tetrabutylammonium iodide, monooctylammonium iodide, dioctylammonium iodide, trioctylammonium iodide, N-octylquinuclidinium iodide, N,N'-dimethyl-N,N'-dihexadecylpiperazinium diiodide, dimethyl-hexadecyl-[3-pyrrolidinylpropyl]ammonium iodide, N,N,N,N',N',N'-hexa(dodecyl)octane-1,8-diammonium diiodide, N,N,N,N',N',N'-hexa(dodecyl)butane-1,4-diammonium diiodide, N-octylpyridinium iodide, and the like.

Exemplary phosphonium compounds include tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(methyl)phosphonium iodide, triphenyl(decyl)phosphonium iodide, triphenyl(dodecyl)phosphonium iodide, tetrakis(2-methylpropyl)phosphonium iodide, tris(2-methylpropyl)(butyl)phosphonium iodide, triphenyl(3,3-dimethylbutyl)phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)(dodecyl)phosphonium iodide, hexyl-tris(2,4,6-trimethylphenyl)phosphonium iodide, tetradecyltris(2,4,6-trimethylphenyl)phosphonium iodide, dodecyltris(2,4,6-trimethylphenyl)phosphonium iodide, and the like.

Tetra-substituted ammonium and phosphonium iodide compounds containing a total of about 16 to 60 carbon atoms are especially preferred. Such compounds have the formulas

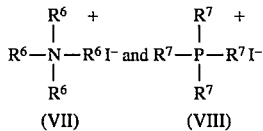

wherein each $R^6$ substituent independently is selected from alkyl of up to about 20 carbon atoms and each $R^7$ substituent is independently selected from $R^6$, benzyl, phenyl or phenyl substituted with up to 3 substituents selected from lower alkyl (alkyl of up to about 4 carbon atoms) lower alkoxy or halogen; or two $R^6$ substituents collectively may represent alkylene of 4 to 6 carbon atoms including alkylene of 4 to 6 carbon atoms substituted with lower alkyl; provided, as specified above, that the quaternary iodide compounds contain about 16 to 60 carbon atoms.

Another group of preferred ammonium iodide compounds are comprised of N-alkyl-azabicycloalkane and N-alkyl- and N,N'-dialkyl-diazabicycloalkane iodide compounds containing 6 to about 12 ring carbon atoms, e.g., bicyclic compounds having the general formula

wherein $R^6$ is defined above and A is the residue of an azabicycloalkane or diazabicycloalkane having 6 to 12 ring carbon atoms (including the 2 carbon atoms in the above general formula), e.g., azabicyclooctane, azabicyclononane, diazabicyclooctane and the like.

Other organic halogen containing compounds which are useful in this invention include neutral, covalently bound halogen compounds such as alkyl halide, including mono- and dihalides containing up to 12 carbon atoms. Specific examples of such alkyl halides include tertiary-butyl bromide, tertiary-butyl iodide, 2-phenyl-2-bromopropane, 1,2-diiodoethane and 9,10-dibromo-9,10-dihydrophenanthroline. If desired, a mixture of 2 or more halogen-containing compounds may be employed as the halogen component of the catalyst.

The catalyst system which is particularly preferred in the process provided by the present invention comprises a combination of (i) quaternary phosphonium iodide compounds containing a total of about 16 to 64 carbon atoms and (ii) organotin iodide compounds having the general formulas:

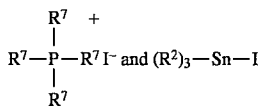

wherein each $R^7$ substituent is independently selected from alkyl of up to about 20 carbon atoms, benzyl, phenyl or phenyl substituted with up to 3 substituents selected from lower alkyl, lower alkoxy or halogen and each $R^2$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen.

The ratio of the onium iodide and Lewis acid components of the catalyst system can vary substantially depending, for example, upon the particular compounds used. Generally, the quaternary onium iodide:Lewis acid mole ratio is within the range of about 100:1 to 0.02:1. For catalyst systems comprising a quaternary onium iodide and an inorganic Lewis acid, the onium iodide:Lewis acid mole ratio preferably is in the range of about 100:1 to 2:1 and most preferably in the range of about 20:1 to 5:1. For catalyst systems comprising a quaternary onium iodide and an organometallic Lewis acid, the onium iodide:Lewis acid mole ratio preferably is in the range of about 20:1 to 0.05:1 and most preferably in the range of about 10:1 to 0.1:1. For the preferred catalyst system comprising a phosphonium iodide and an organotin iodide, a phosphonium iodide:organotin iodide mole ratio of about 5:1 to 0.2:1 is especially preferred.

The amounts of the catalyst components which may be used may vary substantially and depend, at least in part, on the particular catalyst components, vinyl ethylene carbonate compound, temperature, and the mode of operation and residence time, including the degree of conversion desired, being employed. Normally, the catalytically effective amounts of each catalyst component will be within the range of about 0.001 to 1 mole of each component per mole of vinyl ethylene carbonate reactant. Catalyst component:reactant ratios in the range of about 0.1:1 to 1:1 more commonly are used.

The process may be operated with or without an added solvent. Thus, the process may be operated utilizing the reactants and/or the reaction products as the solvent. Examples of suitable optional solvents include aromatic or aliphatic hydrocarbons, e.g., hexane, heptane, benzene, toluene, and xylene isomers; halogenated hydrocarbons, e.g., chlorobenzene and chlorotoluene; ethers, e.g., anisole, dibutyl ether, methyl t-butyl ether and diphenyl ether; amides, e.g., dimethylformamide, dimethylacetamide and N-methylpyrrolidinone; and esters, e.g., isobutyl isobutyrate and phenyl isobutyrate. Additional examples of possible solvents useful in the process are described in U.S. Pat. No. 5,034,545.

The process may be carried out over a wide range of temperatures such as from about 20° to 250° C. with temperatures in the range of about 60° to 150° C. being preferred. Pressure is not an important factor since the process normally may be operated at approximately ambient pressure. However, pressures moderately, e.g., up to 5 bars, above or below atmospheric may be used if desired. The process may be operated in a continuous or batchwise manner. In continuous operation, the vinyl ethylene carbonate reactant is continuously fed to a reactor and the 2,5-dihydrofuran product is removed continuously from the reactor, for example, by vapor stripping, continuous extraction of the catalyst-containing reaction mixture or distillation of the product from the catalyst mixture. Alternatively, the process can be operated in a batchwise mode where the product is isolated from the catalyst by any conventional technique such as vapor stripping, distillation, extraction or crystallization. Although liquid phase operation of the process is described and illustrated herein, the process also may be operated in the gas phase wherein a vinyl ethylene carbonate reactant is fed in the form of a vapor or, possibly, a liquid to a reactor containing one or more beds of the catalyst system described hereinabove. The product 2,5-dihydrofuran compound is removed as a vapor from the reactor. An extensive description of vapor phase operation which may be utilized in the practice of the present invention appears in U.S. Pat. No. 5,082,956.

A particularly preferred embodiment of the present invention concerns the liquid phase preparation of 2,5-dihydrofuran by contacting at a temperature of about 60° to 150° C. vinyl ethylene carbonate (4-ethenyl-1,3-dioxolane-2-one) with a catalyst comprising (1) an acidic component selected from organotin iodide compounds having the general formula:

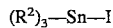

wherein each $R^2$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen; and (2) an iodine component selected from qua-ternary phosphonium iodide compounds containing a total of about 16 to 64 carbon atoms having the general formula:

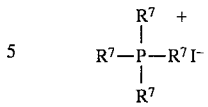

wherein each $R^7$ substituent is independently selected from alkyl of up to about 20 carbon atoms, benzyl, phenyl or phenyl substituted with up to 3 substituents selected from lower alkyl, lower alkoxy or halogen.

The process of the present invention is further illustrated and described by the following examples. The procedure used in the examples involved adding the catalyst components (4.5 millimoles [mmol] of each) under nitrogen to a 50 mL, round bottom flask equipped with a thermometer, stirring bar and heating mantle. Vinyl ethylene carbonate (4-ethenyl-1,3-dioxolane-2-one, 5 mL, 51.4 mmol) and solvent (if used) were added to the flask which then was equipped for simple distillation into a dry ice (solid carbon dioxide) chilled receiver. The contents of the flask then were heated to the reaction temperature (either 120° or 140° C.) for 1 hour unless specified otherwise. The catalyst components, temperature and solvent (if used) in each of Examples 1–42 and Comparative Example C-1 are listed in each of the examples set forth below.

The crude product was distilled as it formed, cooled and analyzed by gas chromatography (GC). The GC analytical results for each example are given as non-normalized, area percentages in Table I wherein "EpB" is 3,4-epoxy-1-butene, "2,3-DHF" is 2,3-dihydrofuran, , "2 5-DHF" is 2,5-dihydrofuran (the desired product), "CrH" is crotonaldehyde, and "VEC" is vinyl ethylene carbonate.

EXAMPLE 1

Zinc chloride; methyl (triphenyl) phosphonium iodide; 120° C.

COMPARATIVE EXAMPLE 1

Zinc chloride; 140° C.

EXAMPLE 2

Tributyltin chloride; tetraphenylphosphonium bromide; 120° C.

EXAMPLE 3

Triphenyltin iodide; tetrabutylammonium bromide; 120° C.

EXAMPLE 4

Triphenyltin iodide; tetra-n-dodecylammonium bromide; 120° C.

EXAMPLE 5

Triphenyltin iodide; 1-iodohexadecane and triphenylphosphine which form in situ hexadecyl(triphenyl)phosphonium iodide; 120° C.; 2-hour reaction time.

EXAMPLE 6

Triphenyltin iodide; sodium iodide; 120° C.

EXAMPLE 7

Triphenyltin iodide; methyl(triphenyl)phosphonium iodide; 120° C.; 5 mL xylene solvent.

EXAMPLE 8

Triphenyltin iodide; methyl(triphenyl)phosphonium iodide; 120° C.; 5 mL N-methylpyrrolidinone solvent.

EXAMPLE 9

47% Aqueous hydrogen iodide; sodium iodide; 120° C.

EXAMPLE 10

Calcium bromide; sodium iodide; methyl(triphenyl)phosphonium iodide; 120° C.

EXAMPLE 11

Copper(I) iodide; methyl(triphenyl)phosphonium iodide; 140° C.

EXAMPLE 12

Manganous chloride; sodium iodide; methyl(triphenyl)phosphonium iodide; 120° C.

EXAMPLE 13

Cesium bromide; methyl(triphenyl)phosphonium iodide; 140° C.

EXAMPLE 14

Zinc iodide; methyl (triphenyl) phosphonium iodide; 140° C.

EXAMPLE 15

Palladium chloride; methyl(triphenyl)phosphonium iodide; 120° C.

EXAMPLE 16

Calcium bromide; sodium iodide; 120° C. 5 mL; N-methyl-pyrrolidinone solvent.

EXAMPLE 17

Uranyl acetate; methyl(triphenyl)phosphonium iodide; 120° C.

EXAMPLE 18

Nickel acetate; methyl(triphenyl)phosphonium iodide; 120° C.

EXAMPLE 19

Copper(II) bromide; methyl(triphenyl)phosphonium iodide; 120° C.

EXAMPLE 20

Aluminum chloride hydrate; methyl(triphenyl)phosphonium iodide; 140° C.

EXAMPLE 21

Cerium(III) chloride; methyl(triphenyl)phosphonium iodide; 120° C.

EXAMPLE 22

Cadmium sulfate; methyl(triphenyl)phosphonium iodide; 140° C.

EXAMPLE 23

Strontium chloride hydrate; methyl(triphenyl)phosphonium iodide; 120° C.

EXAMPLE 24

Magnesium chloride; methyl(triphenyl)phosphonium iodide; 120° C.

EXAMPLE 25

Barium nitrate; methyl(triphenyl)phosphonium iodide; 120° C.

EXAMPLE 26

Thorium nitrate; methyl(triphenyl)phosphonium iodide; 120° C.

EXAMPLE 27

Cobalt (II) chloride hydrate; methyl (triphenyl) phosphonium iodide; 120° C.

EXAMPLE 28

Calcium chloride; sodium bromide; 140° C.

EXAMPLE 29

Calcium chloride; sodium iodide; 120° C.

EXAMPLE 30

Magnesium chloride; sodium iodide; 120° C.

EXAMPLE 31

Calcium bromide; tertiary butyl bromide; 120° C.

EXAMPLE 32

Calcium bromide; tertiary butyl iodide; 120° C.; 5 mL N-methylpyrrolidinone.

EXAMPLE 33

Calcium chloride; benzyl(trimethyl)ammonium chloride; 140° C.

EXAMPLE 34

Triphenyltin iodide; methyl(triphenyl)phosphonium iodide; 120° C.

EXAMPLE 35

Triphenyltin iodide; triphenylphosphonium diiodide (diiodotriphenylphosphorane, 2.4 mmol); 140° C.; 5 mL N-methylpyrrolidinone solvent.

EXAMPLE 36

Bismuth nitrate pentahydrate; methyl(triphenyl)-phosphonium iodide; 140° C.

EXAMPLE 37

Antimony trichloride; methyl(triphenyl)phosphonium iodide; 120° C.

EXAMPLE 38

Zirconium oxychloride hexahydrate; methyl(triphenyl)phosphonium iodide; 120° C.

EXAMPLE 39

Vanadium trichloride; methyl(triphenyl)phosphonium iodide; 120° C.

EXAMPLE 40

Chromium (II) chloride; methyl(triphenyl)phosphonium iodide; 120° C.

EXAMPLE 41

Formic acid; methyl(triphenyl)phosphonium iodide; 140° C.; 0.5 hour reaction time.

EXAMPLE 42

Sulfuric acid; methyl(triphenyl)phosphonium iodide; 140° C.; 0.5 hour reaction time.

TABLE I

| Example | Furan | EpB + 2,3-DHF | 2,5-DHF | CrH | VEC |
|---|---|---|---|---|---|
| 1 | 0.12 | 3.81 | 14.6 | 62.75 | — |
| C-1 | 0.65 | 14.09 | 4.6 | 68.06 | — |
| 2 | 0.3 | 74.71 | 17.31 | 4.81 | — |
| 3 | 0.45 | 0.91 | 95.33 | 2.73 | 0.34 |
| 4 | 0.29 | 0.62 | 97.27 | 0.89 | — |
| 5 | 0.23 | 0.5 | 96.49 | 2.28 | 0.39 |
| 6 | 0.55 | 0.55 | 94.55 | 1.03 | 0.38 |
| 7 | 0.55 | 0.7 | 97.84 | 0.72 | — |
| 8 | 0.36 | 0.61 | 93.8 | 1.99 | 2.56 |
| 9 | 2.04 | 13.74 | 71.44 | 4.83 | 0.9 |
| 10 | 0.2 | 4.67 | 83.69 | 5.85 | — |
| 11 | 0.62 | 1.09 | 76.35 | 14.78 | — |
| 12 | 1.18 | 4.39 | 74.4 | 17.06 | 0.31 |
| 13 | 0.52 | 54.77 | 40.15 | 2.3 | 0.37 |
| 14 | 0.88 | 4.45 | 19.6 | 69.73 | 0.37 |
| 15 | 3.97 | 37.31 | 4.46 | 42.63 | 0.13 |
| 16 | 0.44 | 3.65 | 91.53 | 3.53 | — |
| 17 | 0.51 | 1.27 | 93.31 | 3.17 | 0.17 |
| 18 | — | 5.51 | 57.01 | 16.7 | 1.62 |
| 19 | 3.8 | 3.48 | 13.19 | 69.67 | 3.02 |
| 20 | 0.28 | 7.64 | 71.22 | 13.14 | 0.29 |
| 21 | 0.96 | 3.09 | 83.54 | 10.32 | 0.08 |
| 22 | 1.22 | 90.12 | 3.87 | 1.29 | — |
| 23 | 0.54 | 5.96 | 37.43 | 4.02 | 13.65 |
| 24 | 0.44 | 4.19 | 69.27 | 16.91 | 0.86 |
| 25 | 5.13 | 42.78 | 46.67 | 2.62 | 0.05 |
| 26 | 6.51 | 1.23 | 77.12 | 9.32 | 0.17 |
| 27 | 0.61 | 11.05 | 42.35 | 38.4 | 1.32 |
| 28 | 0.35 | 26.73 | 64.51 | 6.9 | 1.24 |
| 29 | 0.71 | 4.54 | 89.88 | 3.27 | 0.5 |
| 30 | 0.56 | 4.16 | 92.18 | 2.31 | 0.36 |
| 31 | 0.03 | 2.91 | 88.19 | 1.72 | 0.42 |
| 32 | 0.47 | 3.99 | 85.22 | 1.99 | 0.48 |
| 33 | — | 51.45 | 17.12 | 9.35 | 2.74 |
| 34 | 0.39 | 0.83 | 92.26 | 1.92 | 4.08 |
| 35 | 1.43 | 6.52 | 68.91 | 3.76 | 0.84 |
| 36 | 1.36 | 3.49 | 32.17 | 6.54 | 50.48 |
| 37 | 13.9 | 1.77 | 34.71 | 12.65 | 1.84 |
| 38 | 0.34 | 1.56 | 77.02 | 10.69 | 1.84 |
| 39 | 0.72 | 5.82 | 32.74 | 45.16 | 1.79 |
| 40 | 1.4 | 2.83 | 66.63 | 15.74 | 1.34 |
| 41 | 9.19 | 60.78 | 18.87 | 4.63 | 2.03 |
| 42 | 3.95 | 1.35 | 65.82 | 8.23 | 0.19 |

EXAMPLE 43

To a 50 mL, round-bottom flask equipped with a thermometer, stirring bar and distillation head with condenser and dry ice-cooled received were added, under nitrogen, methyl(triphenyl)phosphonium iodide (1.82 g, 4.5 mmol), vinyl ethylene carbonate (5 mL, 51.4 mmol) and N-methylpyrrolidinone solvent (5 mL). The contents of the flask were heated at 140° C. for 1 hour. After the 1 hour of heating, no product had been collected in the receiver.

The reaction mixture was cooled to ambient temperature and uranyl oxyacetate (1.90 g, 4.5 mmol) was added and the reaction mixture was heated at 120° C. for 1 hour. The crude product thus obtained (0.32 g) was analyzed by GC and found to contain (by area percent): furan-0.54%; 3,4-epoxy-1-butene-1.35%; 2,5-dihydrofuran-86.47%; crotonaldehyde-1.60%; and unreacted vinyl ethylene carbonate-9.52%.

EXAMPLE 44

To a 50 mL, round-bottom flask equipped with a thermometer, stirring bar and distillation head with condenser and dry ice-cooled received were added, under nitrogen, triphenyltin iodide (3.37 g, 4.5 mmol), vinyl ethylene carbonate (5 mL, 51.4 mmol) and N-methyl-pyrrolidinone solvent (5 mL). The contents of the flask were heated at 140° C. for 1 hour. After the 1 hour of heating, no product had been collected in the receiver.

The reaction mixture was cooled to ambient temperature and sodium iodide (0.68 g, 4.5 mmol) was added and the reaction mixture was heated at 140° C. for 1 hour. At the end of the second hour of heating, 1.92 g of crude product were obtained. GC analysis showed that the crude product contained (area percent): furan-0.21%; 3,4-epoxy-1-butene-1.07%; 2,5-dihydrofuran-93.96%; crotonaldehyde-2.67%; and unreacted vinyl ethylene carbonate-1.74%.

EXAMPLE 45

To a 250 mL, round-bottom flask equipped with a thermometer, addition funnel, stirring bar and distillation head with condenser and dry ice-cooled received were added, under nitrogen, calcium bromide (5.0 g, 25 mmol), sodium iodide (3.75 g, 25 mmol), and N-methylpyrrolidinone solvent (25 mL, 25.82 g). Vinyl ethylene carbonate (25 mL, 29.68 g, 255 mmol) was charged to the addition funnel and the contents of the flask were heated to 120° C. Upon reaching 120° C. the VEC was added dropwise over a period of 0.5 hour while crude product was distilled from the reaction mixture as it formed. A total of 13.73 g of crude product was collected in the receiver. The contents of the flask were heated at 140° C. for 1 hour. GC analysis showed that the crude product contained (area percent): furan-0.25%; 3,4-epoxy-1-butene-4.81%; 2,5-dihydrofuran-88.61%; crotonaldehyde-4.98%; and unreacted vinyl ethylene carbonate-1.28%. Proton NMR showed that the recovered catalyst solution (38.10 g) contained solvent and unreacted VEC but no oligomer/polymer.

EXAMPLE 46

To a 250 mL, round-bottom flask equipped with a thermometer, addition funnel, stirring bar and distillation head with condenser and dry ice-cooled received were added, under nitrogen, triphenyltin iodide (7.14 g, 15 mmol), tetradodecylammonium iodide (3.75 g, 15 mmol), and N-methylpyrrolidinone solvent (25 mL, 25.82 g). Vinyl ethylene carbonate (15 mL, 18.0 g, 155 mmol) was charged to the addition funnel and the contents of the flask were heated to 120° C. Upon reaching 120° C., the VEC was added dropwise over a period of 0.5 hour while crude product was distilled from the reaction mixture as it formed. The reaction mixture was heated for a total of 3 hours at 120°–130° C. to produce a total of 8.4 g of crude product. GC analysis showed that the crude product contained (area percent): furan-0.26%; 3,4-epoxy-1-butene-0.69%; 2,5-dihydrofuran-91.16%; crotonaldehyde-2.55%; and unreacted vinyl ethylene carbonate-5.19%. Proton NMR showed that the recovered catalyst solution (46.13 g) contained solvent and unreacted VEC but no oligomer/polymer.

The invention has been described in detail with particular reference to preferred embodiments thereof, but it will be understood that variations and modifications can be effected within the spirit and scope of the invention.

We claim:

1. Process for the preparation of a 2,5-dihydrofuran compound having the formula:

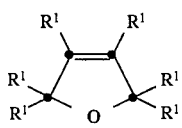  (I)

which comprises contacting a vinyl ethylene carbonate compound having the formula

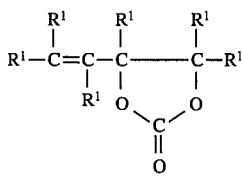  (II)

with a catalyst system comprising an acidic component and a halogen component;

wherein each $R^1$ is independently selected from hydrogen, alkyl of up to about 8 carbon atoms, a carbocyclic or heterocyclic aryl group of about 5 to 10 carbon atoms or halogen or any two $R^1$ substituents collectively may represent an alkylene group forming a ring.

2. Process according to claim 1 wherein the $R^1$ substituents individually represent hydrogen, lower alkyl or collectively represent alkylene of 4 to about 8 carbon atoms; the acidic component of the catalyst is selected from Lewis acids comprising the halides of calcium, zinc, tin, manganese, uranium, aluminum, cerium, magnesium, thorium, zirconium, copper and chromium; and the halogen component of the catalyst is selected from the alkali metal bromides, alkali metal iodides, onium bromides and onium iodides.

3. Process according to claim 2 wherein at least 4 of the $R^1$ groups represent hydrogen; the halogen component of the catalyst is selected from the alkali metal iodides and onium iodides; and the contacting is done at a temperature of about 20° to 250° C.

4. Process according to claim 3 wherein the acidic component of the catalyst is selected from organo tin compounds having the formula

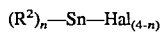

wherein each $R^2$ substituent independently is selected from alkyl of up to about 12 carbon atoms, benzyl, phenyl or phenyl substituted with up to 3 substituents selected from lower alkyl, lower alkoxy or halogen;

Hal is iodo; and n is 2 or 3.

5. Process according to claim 3 wherein the acidic component of the catalyst is selected from organo tin compounds having the formula

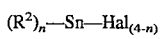

wherein each $R^2$ substituent independently is selected from alkyl of up to about 12 carbon atoms, benzyl, phenyl or phenyl substituted with up to 3 substituents selected from lower alkyl, lower alkoxy or halogen;

Hal is iodo; and n is 2 or 3;

the halogen component is selected from tetra-substituted ammonium and phosphonium iodide compounds containing a total of about 16 to 60 carbon atoms having the formulas

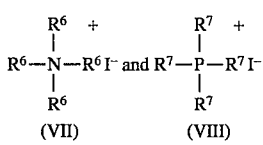

wherein each $R^6$ substituent independently is selected from alkyl of up to about 20 carbon atoms and each $R^7$ substituent is independently selected from $R^6$, benzyl, phenyl or phenyl substituted with up to 3 substituents selected from lower alkyl lower alkoxy or halogen; or two $R^6$ substituents collectively may represent alkylene of 4 to 6 carbon atoms including alkylene of 4 to 6 carbon atoms substituted with lower alkyl; and the contacting is performed at 60° to 150° C.

6. Process for the preparation of a 2,5-dihydrofuran compound having the formula:

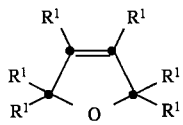  (I)

which comprises contacting at a temperature of about 60° to 150° C. a vinyl ethylene carbonate compound having the formula

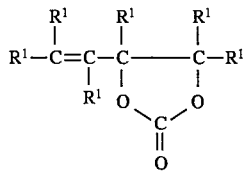  (II)

with a catalyst system comprising a combination of (i) a quaternary phosphonium iodide compound containing a total of about 16 to 64 carbon atoms and (ii) an organotin iodide compound having the general formulas:

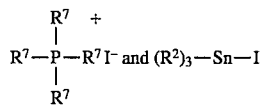

wherein each $R^7$ substituent is independently selected from alkyl of up to about 20 carbon atoms, benzyl, phenyl or phenyl substituted with up to 3 substituents selected from lower alkyl, lower alkoxy or halogen;

each $R^2$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen; and each $R^1$ is independently selected from hydrogen, alkyl of up to about 8 carbon atoms, a carbocyclic or heterocyclic aryl group of about 5 to 10 carbon atoms or halogen or any two $R^1$ substituents collectively may represent an alkylene group forming a ring.

7. Process for the preparation of 2,5-dihydrofuran which comprises contacting at a temperature of about 20° to 250° C. vinyl ethylene carbonate with a catalyst system comprising an acidic component and a halogen component.

8. Process according to claim 7 wherein the acidic component of the catalyst is selected from Lewis acids comprising the halides of calcium, zinc, tin, manganese, uranium, aluminum, cerium, magnesium, thorium, zirconium, copper and chromium; and the halogen component of the catalyst is selected from the alkali metal bromides, alkali metal iodides, onium bromides and onium iodides.

9. Process according to claim 8 wherein the acidic component of the catalyst is selected from organo tin compounds having the formula

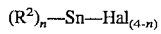

wherein each $R^2$ substituent independently is selected from alkyl of up to about 12 carbon atoms, benzyl, phenyl or phenyl substituted with up to 3 substituents selected from lower alkyl, lower alkoxy or halogen;

Hal is iodo; and n is 2 or 3.

10. Process according to claim 8 wherein the acidic component of the catalyst is selected from organo tin compounds having the formula

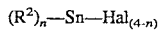

wherein each $R^2$ substituent independently is selected from alkyl of up to about 12 carbon atoms, benzyl, phenyl or phenyl substituted with up to 3 substituents selected from lower alkyl, lower alkoxy or halogen;

Hal is iodo; and n is 2 or 3; and the halogen component is selected from tetra-substituted ammonium and phosphonium iodide compounds containing a total of about 16 to 60 carbon atoms having the formulas

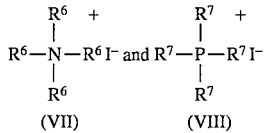

wherein each $R^6$ substituent independently is selected from alkyl of up to about 20 carbon atoms and each $R^7$ substituent is independently selected from $R^6$, benzyl, phenyl or phenyl substituted with up to 3 substituents selected from lower alkyl lower alkoxy or halogen; or two $R^6$ substituents collectively may represent alkylene of 4 to 6 carbon atoms including alkylene of 4 to 6 carbon atoms substituted with lower alkyl; and the process is carried out at a temperature of about 60° to 150° C.

11. Process for the preparation of 2,5-dihydrofuran which comprises contacting in the liquid phase at a temperature of about 60° to 150° C. vinyl ethylene carbonate with a catalyst comprising a combination of (i) a quaternary phosphonium iodide compound containing a total of about 16 to 64 carbon atoms and (ii) an organotin iodide compound having the general formulas:

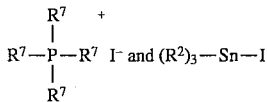

wherein each $R^7$ substituent is independently selected from alkyl of up to about 20 carbon atoms, benzyl, phenyl or phenyl substituted with up to 3 substituents selected from lower alkyl, lower alkoxy or halogen; and each $R^2$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen.

* * * * *